(12) United States Patent
Mitsui et al.

(10) Patent No.: US 7,578,813 B2
(45) Date of Patent: Aug. 25, 2009

(54) DISPOSABLE WEARING ARTICLE

(75) Inventors: Koichiro Mitsui, Kagawa-ken (JP);
Takayuki Miyoshi, Kagawa-ken (JP);
Hironao Minato, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 10/853,238

(22) Filed: May 26, 2004

(65) Prior Publication Data
US 2004/0243091 A1 Dec. 2, 2004

(30) Foreign Application Priority Data
May 27, 2003 (JP) .............................. 2003-149372
May 7, 2004 (JP) .............................. 2004-139126

(51) Int. Cl.
*A61F 13/62* (2006.01)
*A61F 13/51* (2006.01)

(52) U.S. Cl. .............. 604/391; 604/385.28; 604/385.29
(58) Field of Classification Search ......... 604/386–391, 604/385.03
See application file for complete search history.

(56) References Cited

U.S. PATENT DOCUMENTS

| | | | | |
|---|---|---|---|---|
| 3,848,594 A | * | 11/1974 | Buell | 604/390 |
| 3,999,545 A | * | 12/1976 | Milnamow | 604/390 |
| 4,846,815 A | * | 7/1989 | Scripps | 604/391 |
| 5,019,065 A | * | 5/1991 | Scripps | 604/385.21 |
| 5,176,671 A | * | 1/1993 | Roessler et al. | 604/391 |
| 5,279,604 A | * | 1/1994 | Robertson et al. | 604/389 |
| 5,537,722 A | * | 7/1996 | Niederhofer et al. | 24/304 |
| 5,611,789 A | * | 3/1997 | Seth | 604/391 |
| 6,007,527 A | * | 12/1999 | Kawaguchi et al. | 604/386 |
| 6,068,620 A | * | 5/2000 | Chmielewski | 604/378 |
| 6,692,477 B2 | * | 2/2004 | Gibbs | 604/386 |
| 6,740,071 B2 | * | 5/2004 | Gibbs | 604/392 |
| 2003/0109844 A1 | * | 6/2003 | Gibbs | 604/389 |

FOREIGN PATENT DOCUMENTS

| | | |
|---|---|---|
| JP | 50-36254 | 4/1975 |
| JP | 9-191908 | 7/1997 |
| JP | 10137008 A * | 5/1998 |
| WO | WO 9728774 A1 * | 8/1997 |

* cited by examiner

*Primary Examiner*—Karin M Reichle
(74) *Attorney, Agent, or Firm*—Lowe Hauptman Ham & Berner, LLP (57) ABSTRACT

A disposable wearing article is provided with a pair of tape fasteners each composed of inner and outer tape strips and a hook member. The outer tape strip has a proximal portion fixed to the side section of the rear waist region and a distal portion extending outwards from the side section. The inner tape strip has a proximal portion fixed to the side section, a first distal portion bonded to the distal portion of the outer tape strip, and a second distal portion extending outwards from the distal portion of the outer tape strip. The hook member is attached to at least the second distal portion of the inner tape strip. The tape fastener has first and second zones corresponding to the distal portions of the outer and inner tape strips. A stiffness of the second zone is lower than that of the first zone.

2 Claims, 6 Drawing Sheets

DISPOSABLE WEARING ARTICLE

RELATED APPLICATIONS

The present application claims the benefit under 35 U.S.C. §119(a) of Japanese Application Serial Number 2003-149372, filed May 27, 2003 and Japanese Application Serial Number 2004-139126, filed May 7, 2004, the disclosures of which are hereby incorporated by reference herein in their entireties.

BACKGROUND OF THE INVENTION

The present invention relates to disposable wearing articles for absorption and containment of bodily discharges and, more particularly, to such articles having a fastening means for connection of front and rear waist regions.

There is disclosed in Japanese Laid-Open Patent Application No. Hei9-191908 a disposable diaper provided with a mechanical fastening means for connection of front and rear waist regions. The mechanical fastening means comprises a hook member bonded on a base tape which is attached on a transversely opposite side section of a rear waist region transversely extending outwardly therefrom and a target tape strip having a plurality of loops for releasably engaging with the hook member and attached on the outer surface of the front waist region.

There is disclosed in Japanese Laid-Open Patent Application No. Sho50-36254 a disposable diaper provided with an adhesive fastening means for connection of front and rear waist regions. The adhesive fastening means comprises a tape fastener having an adhesive layer applied on a base tape which is attached on the outer surface of a side section of the rear waist region transversely extending outwardly therefrom and a second tape shorter than the tape fastener which is attached on the inner surface of the side section of the rear waist region and connected to the tape fastener so as to form a Y-shape connection cooperatively with the tape fastener.

The diaper disclosed in Hei9-191908 has a problem that the target tape strip is apt to be irregularly deformed by its flexion and/or distortion occurring due to the movement of the wearer. Such a flexion and/or a distortion of the target tape strip may lead to disengagement of a proximal portion of the tape fastener from the loops and/or to release of the proximal portion of the tape fastener from the side section. The tape fastener is formed from a single sheet and, if a peel strength of the proximal portion relative to the side sections is correspondingly low, it is likely that a distal portion of the tape fastener might be irregularly moved due to the flexion and/or distortion of the target tape strip during use of the diaper and, in consequence, a peeling force and/or a shearing force generated by a movement of the distal portion might be exerted upon the proximal portion, eventually resulting in separation of the proximal portion from the side section.

In the known diaper, an intermediate zone extends between the proximal portion and the hook member of the distal portion. The intermediate zone of a relatively low stiffness may be unacceptably moved. Such movement of the intermediate zone may cause a peeling force and/or a shearing force to exert upon the proximal portion and thereby further facilitate the proximal portion to be peeled off the side section. If zones of the distal portion carrying the hook member permanently bonded thereto have an unacceptably high stiffness, the hook member carrying zones may be unable to follow the movement of the target tape strip. In other words, the hooks may be unable to follow the movement of the loops, so there is a possibility that the hooks might be unintentionally disengaged from the loops during use of the diaper.

In the diaper disclosed in Sho50-36254, if a hook member bonded on the base tape is used for the tape fastener having the adhesive layer applied on the base tape, a portion on which the hook member is attached will have a higher stiffness than the adhesive tape fastener. Consequently, the diaper having such a tape fastener will be accompanied with as a problem as the diaper of Hei9-191908.

SUMMARY OF THE INVENTION

A disposable wearing article includes: a first surface and a second surface opposite to the first surface; first and second waist regions, and a crotch region extending in a longitudinal direction of the article between the first and second waist regions; a liquid-pervious topsheet adapted to face a wearer's body in use; a liquid-impervious backsheet adapted to face away from the wearer's body in use; a liquid-absorbent core interposed between the topsheet and the backsheet; a pair of water-resistant, longitudinal barrier cuffs each including: a moveable portion biased to rise above the core, and a fixed portion extending in a transverse direction of the article outwardly from an adjacent one of transversely opposite side edges of the core; a pair of tape fasteners extending in the transverse direction outwardly from transversely opposite side sections of first waist region, respectively.

Each the tape fastener includes first and second monolithic tape strips disposed on the respective side section so as to sandwich the respective side section therebetween, and a hook member attached on one of the first and second monolithic tape strips; and a target zone disposed on the first surface in the second waist region and having a plurality of loops releasably engageable with a plurality of hooks of the hook members of the tape fasteners.

In each of the tape fasteners, the first monolithic tape strip consists of: a proximal portion permanently bonded to the first surface in the first waist region at the associated side section, and a distal portion contiguous with the proximal portion and extending in the transverse direction outwardly from the associated side section, the second monolithic tape strip consists of: a proximal portion permanently bonded to the second surface in the first waist region at the associated side section, a first distal portion contiguous with the proximal portion of the second monolithic tape strip, extending in the transverse direction outwardly from the associated side section, and being permanently, directly bonded to the distal portion of the first monolithic tape strip, and a second distal portion contiguous with the first distal portion, extending in the transverse direction further outwardly beyond an outermost end of the distal portion of the first monolithic tape strip, and being free of direct attachment to the first monolithic tape strip.

The proximal portions of the first and second monolithic tape strips are permanently bonded to and sandwich therebetween the associated side section which is defined by the backsheet and the fixed portion of an associated one of the barrier cuffs.

The hook member is permanently, directly bonded to both the first and second distal portions of the second monolithic tape strip, and is free of direct attachment to the proximal portion of the second monolithic tape strip, whereby the hooks of the hook member are distributed over the first and second distal portions, but not over the proximal portion, of the second monolithic tape strip.

Each the tape fastener has a stiffness lower in a second zone where the second distal portion of the second monolithic tape strip extends than in a first zone where the distal portion of the first monolithic tape strip extends.

Each the tape fastener has a Gurley stiffness in a range of 5.0 to 12 mN in the first zone and a Gurley stiffness in a range of 0.3 to 4.6 mN in the second zone.

In each of the tape fasteners, the hook member provided on the second distal portion has an area in a range of 1.75 to 8.0 cm$^2$. An entire dimension, as measured in the transverse direction of the article, of each of the distal portion of the first monolithic tape strip and the first distal portion of the second monolithic tape strip is in a range of 8 to 15 mm; and an entire dimension, as measured in the transverse direction of the article, of the second distal portion of the second monolithic tape strip is in a range of 17 to 22 mm.

A disposable wearing article includes: a first surface and a second surface opposite to the first surface; first and second waist regions, and a crotch region extending in a longitudinal direction of the article between the first and second waist regions; a liquid-pervious topsheet adapted to face a wearer's body in use; a liquid-impervious backsheet adapted to face away from the wearer's body in use; a liquid-absorbent core interposed between the topsheet and the backsheet; a pair of water-resistant, longitudinal barrier cuffs each including: a moveable portion biased to rise above the core, and a fixed portion extending in a transverse direction of the article outwardly from an adjacent one of transversely opposite side edges of the core; a pair of tape fasteners extending in the transverse direction outwardly from transversely opposite side sections of first waist region, respectively.

Each the tape fastener includes first and second monolithic tape strips disposed on the respective side section so as to sandwich the respective side section therebetween, and a hook member attached on one of the first and second monolithic tape strips; and a target zone disposed on the first surface in the second waist region and having a plurality of loops releasably engageable with a plurality of hooks of the hook members of the tape fasteners.

In each of the tape fasteners, the first monolithic tape strip consists of: a proximal portion permanently bonded to the first surface in the first waist region at the associated side section, and a distal portion contiguous with the proximal portion and extending in the transverse direction outwardly from the associated side section, the second monolithic tape strip consists of: a proximal portion permanently bonded to the second surface in the first waist region at the associated side section, a first distal portion contiguous with the proximal portion of the second monolithic tape strip, extending in the transverse direction outwardly from the associated side section, and being permanently, directly bonded to the distal portion of the first monolithic tape strip, and a second distal portion contiguous with the first distal portion, extending in the transverse direction further outwardly beyond an outermost end of the distal portion of the first monolithic tape strip, and being free of direct attachment to the first monolithic tape strip.

The proximal portions of the first and second monolithic tape strips are permanently bonded to and sandwich therebetween the associated side section which is defined by the backsheet and the fixed portion of an associated one of the barrier cuffs.

The hook member is permanently, directly bonded to both the first and second distal portions of the second monolithic tape strip, and is free of direct attachment to the proximal portion of the second monolithic tape strip, whereby the hooks of the hook member are distributed over the first and second distal portions, but not over the proximal portion, of the second monolithic tape strip.

Each the tape fastener has a stiffness lower in a second zone where the second distal portion of the second monolithic tape strip extends than in a first zone where the distal portion of the first monolithic tape strip extends.

Each the tape fastener has a Gurley stiffness in a range of 5.0 to 12 mN in the first zone and a Gurley stiffness in a range of 0.3 to 4.6 mN in the second zone.

In each of the tape fasteners, a dimension of the proximal portion of the second monolithic tape strip in the transverse direction of the article is greater than that of the proximal portion of the first monolithic tape strip.

The hook member provided on the second distal portion has an area in a range of 1.75 to 8.0 cm$^2$. An entire dimension, as measured in the transverse direction of the article, of each of the distal portion of the first monolithic tape strip and the first distal portion of the second monolithic tape strip is in a range of 8 to 15 mm; and an entire dimension, as measured in the transverse direction of the article, of the second distal portion of the second monolithic tape strip is in a range of 17 to 22 mm.

DETAILED DESCRIPTION OF THE PREFERRED EMBODIMENTS

Details of a disposable wearing article according to the present invention will be more fully understood from the description given hereunder with reference to the accompanying drawings.

Figure 1:
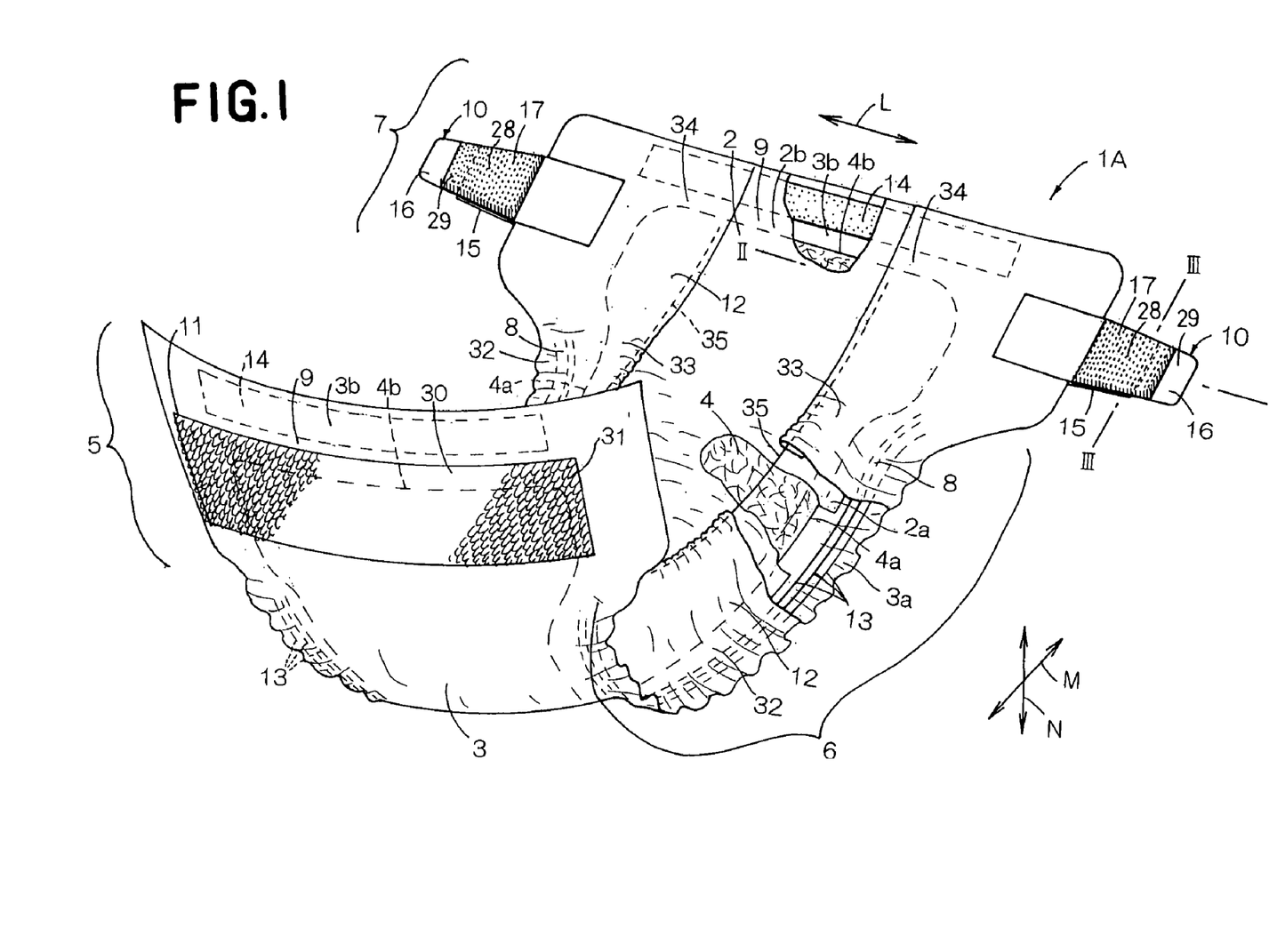
FIG. 1 is a partially cutaway perspective view depicted a disposable wearing article according to one embodiment of the invention.
Figure 2:
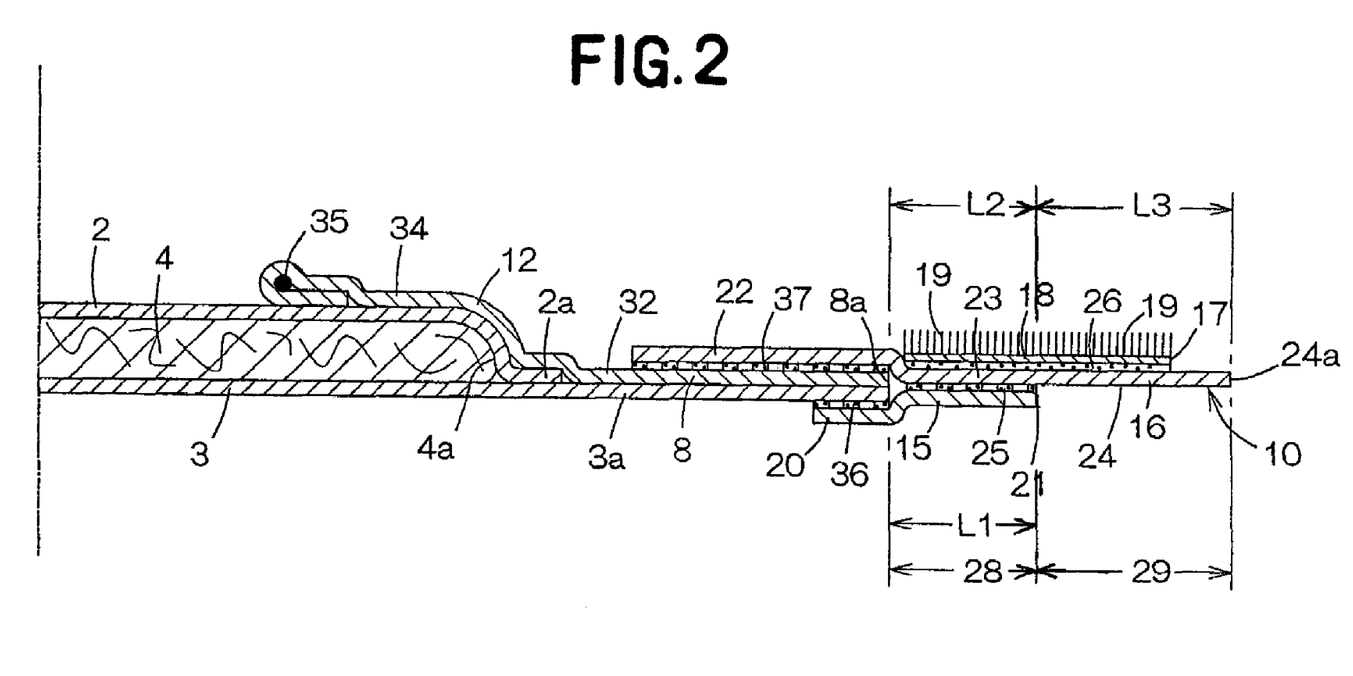
FIG. 2 is a sectional view taken along the line II-II in FIG. 1.
Figure 3:
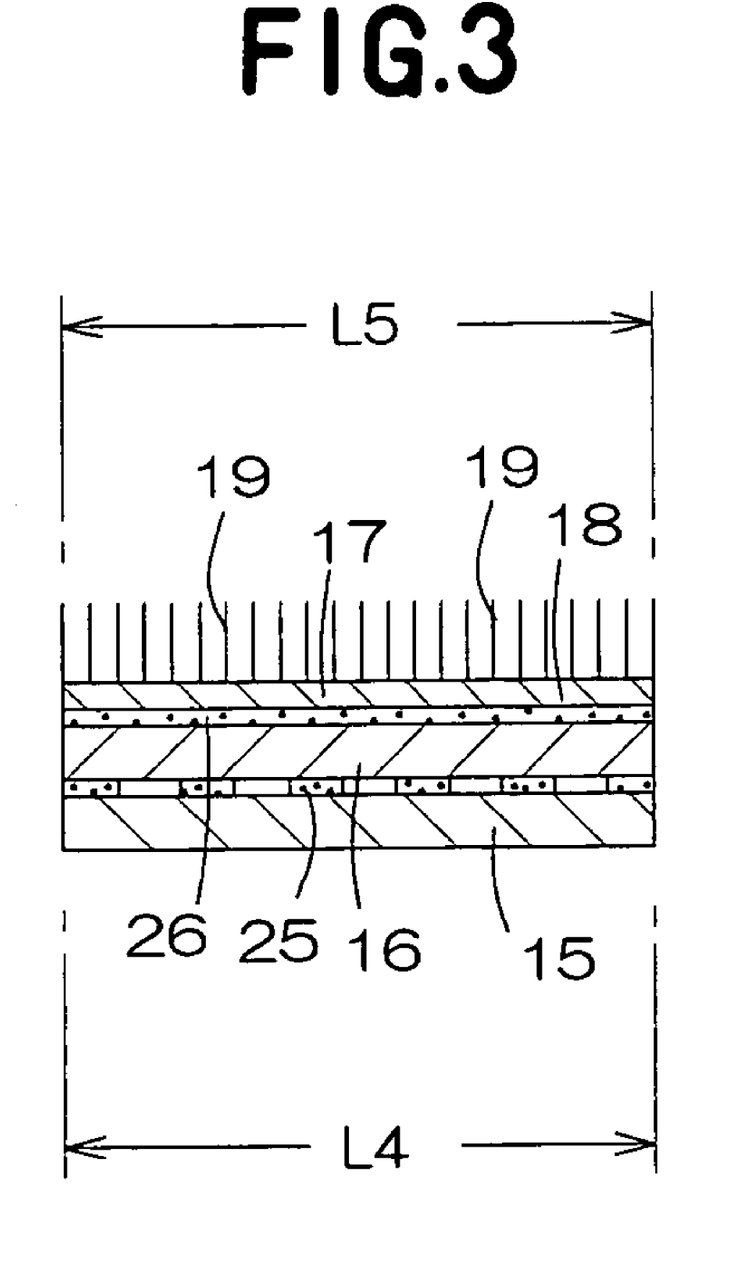
FIG. 3 is a sectional view taken along the line III-III in FIG. 1.

FIG. 1 is a partially cutaway perspective view depicting a diaper according to one embodiment of the invention. FIG. 2 is a sectional view taken along the line II-II in FIG. 1. FIG. 3 is a sectional view taken along the line III-III in FIG. 1. In FIG. 1, a transverse direction is indicated by an arrow L, a longitudinal direction is indicated by an arrow M and a thickness direction is indicated by an arrow N.

A diaper 1A comprises a liquid-pervious topsheet 2 facing the wearer's skin, a liquid-impervious backsheet 3 facing away from the wearer's skin and a liquid-absorbent core 4 interposed between these sheets 2, 3. The diaper 1A has, as viewed in the longitudinal direction, a front waist region 5, a rear waist region 7 and a crotch region 6 extending between these waist regions 5, 7. The diaper 1A further comprises a pair of side flaps 8, which function as gasket cuffs about the wearer's legs, lying outside transversely opposite side edges 4a of the core 4 and extending in the longitudinal direction and a pair of end flaps 9 lying outside longitudinal opposite ends 4b of the core 4 and extending in the transverse direction. The core 4 extends between the front and rear waist regions 5, 7 and is permanently bonded between the top- and backsheets 2, 3. In the crotch region 6, the side flaps 8 describe circular arcs which are convex inward in the transverse direction of the diaper 1A. Thus, the diaper 1A has a generally hourglass-like planar shape.

The rear waist region 7 is provided on the side flaps 8 with a pair of tape fasteners 10, respectively, extending in the transverse direction while the front waist region 5 is provided with a target zone 11 defined by an elongate sheet attached thereon extending in the transverse direction. The side flaps 8 are provided with a pair of liquid-impervious leak-barrier cuffs 12, respectively, extending in the longitudinal direction between the front and rear waist regions 5, 7. In the crotch region 6, a plurality of thread- or ribbon-like leg elastic members 13 extending in the longitudinal direction are attached to the respective side flaps 8 so as to be contractible in this longitudinal direction. The end flaps 9 are respectively provided with tape-like waist elastic members 14 extending in the transverse direction so as to be contractible in this transverse direction.

The tape fasteners 10 each comprises outer and inner tape strips 15, 16 extending parallel to each other in the transverse direction and hook member 17 extending on the inner tape strip 16 also in the transverse direction. The outer tape strip 15 is made of a plastic film or a fibrous nonwoven fabric. The inner tape strip 16 is made of a fibrous nonwoven fabric. The hook members 17 each comprises a hook backing 18 and a plurality of hooks 19 protruding from the hook backing 18. The hook member 17 is made of a plastic material.

The outer tape strip 15 has a proximal portion 20 permanently bonded to the outer surface of the associated side flap 8 and a distal portion 21 being contiguous to the proximal portion 20 and extending outward from a side edge 8a of this side flap 8 in the transverse direction. The inner tape strip 16 has a proximal portion 22 permanently bonded to the inner surface of the associated side flap 8, a first distal portion 23 being contiguous to the proximal portion 22 and extending outward from the side edge 8a of this side flap 8 and a second distal portion 24 being contiguous to the first distal portion 23 and extending outward from the distal portion 21 of the outer tape strip 15 in the transverse direction. Thus, the associated side flap 8 is bonded between the respective proximal portions 20, 22 of the inner and outer tape strips 15, 16, which are bonded to each other at the distal portion 21 of the outer tape strip 15 and the first distal portion 23 of the inner tape strip 16 in a Y-shape. Though not shown in Figures, the proximal portion 20 of the outer tape strip 15 may be bonded on the inner surface of the associated side flap 8 and the proximal portion 22 of the inner tape strip 16 may be bonded on the outer surface of the associated side flap 8.

A longitudinal dimension L4 (i.e., a width) of each of the outer tape strips 15 as measured in the proximal portion 20 and the distal portion 21 is generally the same as a longitudinal dimension L5 (i.e., a width) of each of the inner tape strips 16 as measured in the proximal portion 22 and the distal portions 23, 24. The inner surfaces of the distal portions 21 of the outer strips 15 are intermittently and permanently bonded to the outer surfaces of the first distal portions 23 of the inner tape strips 16 by means of adhesives 25.

The hook members 17 each is provided on the inner tape strip 16 so as to cover a generally entire area of the first distal portion 23 as well as the partial area of the second distal portion 24 except a tab 24a thereof. That is, the hook member 17 extends over a generally entire dimension of the first distal portion 23 in the transverse direction and extends over generally entire dimensions of the first and second distal portions 23, 24 in the transverse direction except the tab 24a. The hook backing 18 of each of the hook members 17 has its inner surface permanently bonded to the outer surface of the first and second distal portions 23, 24 by means of adhesives 26. The tab 24a of the second distal portion 24 is defined as a finger-grip for the tape fastener 10.

The tape fasteners 10 each has a first zone 28 in which the distal portion 21 of the outer tape strip 15 as well as the first distal portion 23 of the inner tape strip 16 extend and a second zone 29 in which the second distal portion 24 of the inner tape strip 16 extends. The first zone 28 is defined by the inner and outer tape strips 15, 16 and the hook member 17 and the second zone 29 is defined by the inner tape strip 16 and the hook member 17. In such a manner that the outer tape strip 15 does not extend outer the second zone 29, the tape fastener 10 has a stiffness higher in the first zone 28 than in the second zone 29.

The target zone 11 has a rectangular planar shape which is relatively long in the transverse direction and comprises a loop backing 30 and a plurality of loops 31 protruding from the loop backing 30. The target zone 11 is made of a plastic material, the loop backing 30 of this target zone 11 has its inner surface permanently bonded to the outer surface of the backsheet 3 by means of adhesives (not shown). While the loops 31 are illustrated by FIG. 1 as partially left out, it should be understood that these loops 31 are provided on the entire outer surface of the loop backing 30.

The leak-barrier cuffs 12 each has a proximal lateral portion 32 lying on the associated side flap 8 and extending in the longitudinal direction, a distal portion 33 normally biased to rise up above the topsheet 2 and extending in the longitudinal direction, and longitudinally opposite end portions 34 lying on the respective end flaps 9 and collapsed inwardly in the transverse direction of the diaper 1A. A stretchable elastic member 35 extending in the longitudinal direction is contractibly attached to the distal portion 33 in the vicinity of its uppermost edge. The elastic member 35 is permanently bonded to the distal portion 33 in a manner that the elastic member 35 is wrapped with a part of the distal portion 33. The elastic member 35 contracts as the diaper 1A curves in the longitudinal direction with the topsheet 2 inside and thereupon the distal portion 33 of the leak-barrier cuffs 12 rises up above the topsheet 2. Consequently, the distal portion 33 forms a barrier against bodily discharges.

The side flaps 8 are formed from transversely opposite lateral portions 2a, 3a of the top- and backsheets 2, 3 extending outwardly beyond the transversely opposite side edges 4a of the core 4 in the transverse direction and the proximal portions 32 of the respective leak-barrier cuffs 12. The lateral portions 2a of the topsheet 2 extend outwardly slightly beyond the transversely opposite side edges 4a of the core 4 and the proximal portions 3a of the backsheet 3 as well as the lateral portions 32 of the leak-barrier cuffs 12 further extend outward beyond the lateral portions 2a in the transverse direction. These portions 2a, 3a, 32, respectively, are placed one upon another and permanently bonded one to another along each pair of the opposed surfaces thereof. Leg elastic members 13 are interposed between the lateral portions 3a of the backsheet 3 and the distal portions 32 of the leak-barrier cuffs 12, respectively, and permanently bonded to the opposite surfaces of these backsheet 3 and the cuffs 12, respectively.

In each of the side flaps 8, the proximal portion 20 of the outer tape strip 15 has its inner surface bonded to the outer surface of the backsheet 3 by means of adhesives 36 and the proximal portion 22 of the inner tape strip 16 has its outer surface bonded to the inner surfaces of the leak-barrier cuffs 12 by means of adhesives 37.

The end flaps 9 are formed from longitudinally opposite end portions 2b, 3b of the top- and backsheets 2, 3 extending outwardly beyond the longitudinally opposite ends 4b of the core 4 in the longitudinal direction. In the end flaps 9, the longitudinally opposite end portions 2b, 3b of the top- and backsheets 2, 3 are placed one upon another and permanently bonded one to another along the opposed surfaces thereof. Waist elastic members 14 are interposed between the end portions 2b of the topsheet 2 and the end portions 3b of the backsheet 3 and permanently bonded to the opposed surfaces of these sheets 2, 3, respectively. The longitudinally opposite end portions 34 of the respective leak-barrier cuffs 12 are permanently bonded to the outer surface of the topsheet 2.

To put the diaper 1A on the wearer's body, the side flaps 8 in the rear waist region 7 are placed from outside upon the side flaps 8 in the front waist region 5 and then the tape fasteners 10 are anchored on the target zone 11 whereby to connect the front waist region 5 and the rear waist region 7 with each other. To anchor the tape fasteners 10 on the target zone 11, the first and second zones 28, 29 are pressed against the target zone 11 with the tab 24a of the tape fasteners 10 by the wearer's fingers so as to bring the hooks 19 in engagement with the loops 31. The diaper 1A is formed with a waist-hole and a pair of leg-holes (not shown) as the front and rear waist regions 5, 7 are connected with each other in this manner. Body fluids discharged from the wearer are absorbed by the core 4 through the topsheet 2 and contained therein.

The tape fasteners 10 each comprises the outer tape strip 15 and the inner tape strip 16 wherein the proximal portions 20, 22 of these tape strips 15, 16 are permanently bonded to the associated side flap 8 interposed between these two tape strips 15, 16, as has previously been described. Such an arrangement advantageously improves a peel strength as well as a shear strength of the tape fastener 10 relative to the side flaps 8 in comparison with the conventional tape fastener formed from a single tape strip.

An irregular deformation of the target zone 11 due to its flexion and/or distortion may be caused by the movement of the wearer. However, the tape fasteners 10 each has a stiffness in its second zone 29 sufficiently low to ensure that the second zone 29 can follow any flexion and/or any distortion of the target zone 11. In other words, the hooks 19 distributed on the second distal portion 24 of the inner tape strip 16 can smoothly move substantially in sync with the movement of the loops 31 on the target zone 11 and therefore it is unlikely that the hooks 19 might be unintentionally disengaged from the loops 31 during use of the diaper 1A. With this diaper 1A, the connection between the front and rear waist regions 5, 7 can be reliably maintained even when the wearer vigorously moves.

While the second zones 29 each can move substantially in sync with flexion and/or distortion of the target zone 11, such a movement of the second zone 29 is restricted by the first zone 28 since the tape fasteners 10 each has a stiffness higher in the first zone 28 than in the second zone 29. Thus, the first zones 28 each makes it difficult that a movement of the second zone 29 to be transmitted to the proximal portions 20, 22 and thereby alleviates a peeling force and/or a shearing force which might be exerted on these proximal portions 20, 22. In other words, there is no anxiety that these proximal portions 20, 22 might be peeled off the side flaps 8. In this way, this diaper 1A can reliably prevent the tape fasteners 10 being peeled off from the side flaps 8.

The hook members 17 each is attached to the inner tape strip 16 not only on the second distal portion 24 but also on the first distal portion 23 so that the hooks 19 on the second distal portion 24 may come in engagement with the loops 31 and simultaneously the hooks 19 on the first distal portion 23 may come in engagement with the loops 31. The first zone 28 of each of the tape fastener 10 is anchored on the target zone 11 by means of the hooks 19 and the first zone 28 has a sufficiently high stiffness to restrain a flexion and/or a distortion of the target zone 11. As a result, it is reliably ensured that such flexion and/or distortion of the target zone 11 might be transmitted to the proximal portions 20, 22 of the inner and outer tape strips 15, 16, respectively.

The first zones 28 each has a Gurley stiffness in a range of 5.0 to 12 mN and the second zones 29 each has a Gurley stiffness in a range of 0.3 to 4.6 mN. If the first zone 28 has a Gurley stiffness lower than 5.0 mN, it will be impossible for the first zone 28 to restrain the movement of the second zone 29 and thereby to alleviate a peeling force and/or a shearing force exerted on the proximal portions 20, 22 because a movement of the second zone 29 will be transmitted to the proximal portions 20, 22 without attenuation via the first zone 28. It will be also impossible for the first zone 28 to restrain a flexion and/or distortion occurring in a region of the target zone 11 placed upon the first zone 28. If the first zones 28 each has a Gurley stiffness exceeding 12 mN, the first zone 28 will be excessively hardened and the wearer will experience an uncomfortable irritation as the first zone 28 comes in contact with the wearer's skin. If the second zones 29 each has a Gurley stiffness lower than 0.3 mN, a flexion and/or a distortion of the target zone 11 may lead to breakage of the second zone 29. If the second zones 29 each has a Gurley stiffness exceeding 4.6 mN, it will be impossible for the second zone 29 to follow any flexion and/or distortion of the target zone 11 and therefore it will be impossible for the hooks 19 on the second zone 29 to move in sync with a movement of the loops 31. Consequently, the hooks 19 may be disengaged from the loops 31 during use of the diaper 1A.

Of each of the tape fastener 10, the outer tape strip 15 preferably has a Gurley stiffness in a range of 0.01 to 0.35 mN, the inner tape strip 16 preferably has a Gurley stiffness in a range of 0.3 to 0.55 mN and the hook member 17 preferably has a Gurley stiffness in a range of 0.28 to 0.32 mN. If the outer tape strips 15 each has a Gurley stiffness lower than 0.01 mN, the inner tape strip 16 has a Gurley stiffness lower than 0.3 mN and the hook member 17 has a Gurley stiffness lower than 0.28 mN, the first zone 28 will have a Gurley stiffness lower than 5.0 mN and the movement of the second zone 29 will be transmitted to the proximal portions 20, 22 via the first zone 28 without attenuation. If the inner tape strip 16 has a Gurley stiffness exceeding 0.55 mN and the tape strip 17 has a Gurley stiffness exceeding 0.32 mN, the second zone 29 will have a Gurley stiffness exceeding 4.6 mN and it will be impossible for the second zone 29 to follow a flexion and/or a distortion of the target zone 11. The Gurley stiffness of the first and second zones 28, 29 of each of the tape fasteners 10 and the Gurley stiffness of each of the inner and outer tape strips 15, 16 and each of the hook members 17 were measured by a method as follows:

(1) The first and second zones 28, 29 of the tape fastener 10 were cut away from the diaper 1A to prepare samples of these first and second zones 28, 29 for measurement of Gurley stiffness. In addition, samples of the outer tape strip 15, the inner tape strip 16 and the hook member 17 for measurement of Gurley stiffness were also prepared. Each of these samples was dimensioned to have a length of approximately 38 mm and a width of approximately 25 mm.

(2) Measurement of Gurley stiffness was carried out using the Gurley's stiffness tester according to the procedures as follow: (a) one end of the sample is held by chuck of the tester in such a manner that the other end is maintained in engagement with a pivot rod of a pendulum; (b) the tester is initialized by loading an auxiliary weight so that the tester scale may point a reading in a range of 3 to 6; and (c) the tester is turn on and a scale reading of the moment at which the pivot rod of the pendulum is separated from the sample is record. Scale reading is recorded both for rightward test and leftward test.

(3) The Gurley stiffness is calculated by an equation of (a scale reading for rightward stiffness+a scale reading for leftward stiffness/2)×{(A×1+B×2+C×3)/5}×(longitudinal dimension (inch) of the sample/transverse dimension (inch)× 9.88, where A, B and C respective represent positions of openings in which the respective weights are loaded, specifically A represents g at a reading of 1 inch, B represent g at a reading of 2 inches and C represents g at a reading of 3 inches. After calculation according to such equation, the Gurley stiffness is converted in N (Newton) unit.

In the tape fastener 10, an area of the hook member 17 lying on the second distal portion 24 of the inner tape strip 16 is in a range of 1.75 to 8.0 cm$^2$. If this area is smaller than 1.75 cm$^2$, the number of the hooks 19 to be engaged with the loops 31 in the second zone 29 will be insufficient to ensure a desired engagement between the second zone 29 of the tape fastener 10 and the target zone 11. With a consequence, a flexion and/or a distortion of the target zone 11 may cause the hooks 19 distributed in the second zone 29 to be disengaged from the loops 31.

In each of the preferred tape fasteners 10, the distal portion 21 of the outer tape strip 15 and the first distal portion 23 of the inner tape strip 16 respectively have transverse dimensions L1, L2 (i.e., a length dimension) both in a range of 8 to 15 mm, the second distal portion 24 of the inner tape strip 16 has a transverse dimension L3 (i.e., a length dimension) in a range of 17 to 22 mm (this dimension L3 includes a dimension 10 mm or of the tab 24a), the distal portion 21 of the outer tape strip 15 has a longitudinal dimension L (i.e., a width dimension) in a range of 25 to 45 mm and the first and second distal portions 23, 24 of the inner tape strip 16 have a longitudinal dimension L5 (i.e., a width dimension) in a range of 25 to 45 mm.

It is also preferable that a length dimension of the proximal portion 22 of the inner tape strip 16 in the transverse direction of the diaper is greater than that of the proximal portion 20 of the outer tape strip 15.

If the transverse dimension L3 is less than 17 mm and the longitudinal dimension L5 is less than 25 mm, the area of the hook member 17 extending over the second distal portion 24 will be smaller than 1.75 cm$^2$ and the second zone 29 of the tape fastener 10 can not be sufficiently engaged with the target zone 11. As a result, a flexion and/or a distortion of the target zone 11 may cause the hooks 19 distributed in the second zone 29 to be disengaged from the loops 31. If the transverse dimensions L1, L2 are less than 8 mm and the longitudinal dimensions L4, L5 are less than 25 mm, the area of the first zone 28 will be insufficient to assure a desired stiffness of the first zone 28. It is impossible for the first zone 28 having its stiffness unacceptably limited in this manner to restrain a movement of the second zone 29. Consequently, the movement of the second zone 29 will be transmitted to the proximal portions 20, 22 via the first zone 28 without attenuation.

Figure 4:
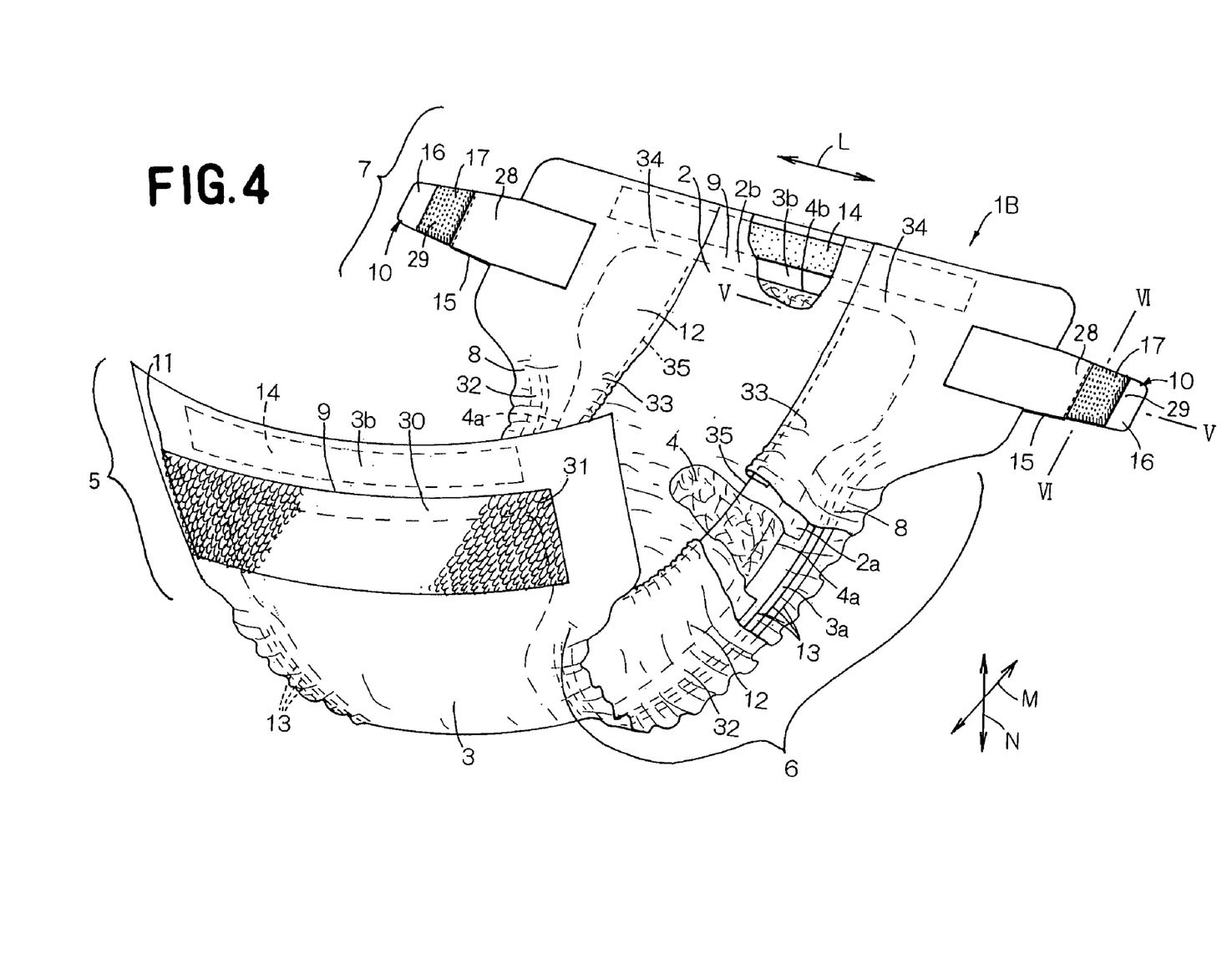
FIG. 4 is a partially cutaway perspective view depicted a disposable wearing article according to another preferred embodiment of the invention.
Figure 5:
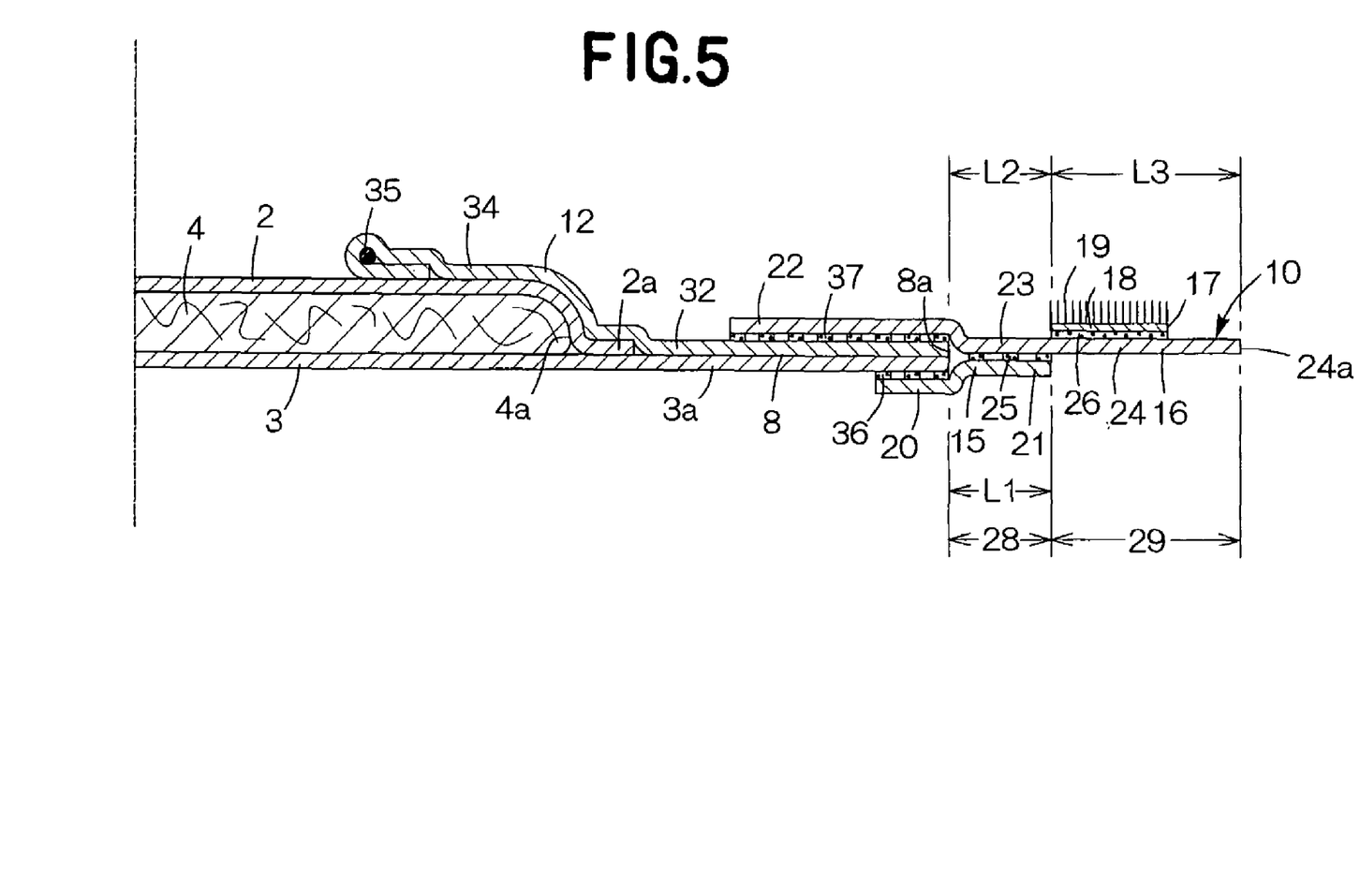
FIG. 5 is a sectional view taken along the line V-V in FIG. 4.
Figure 6:
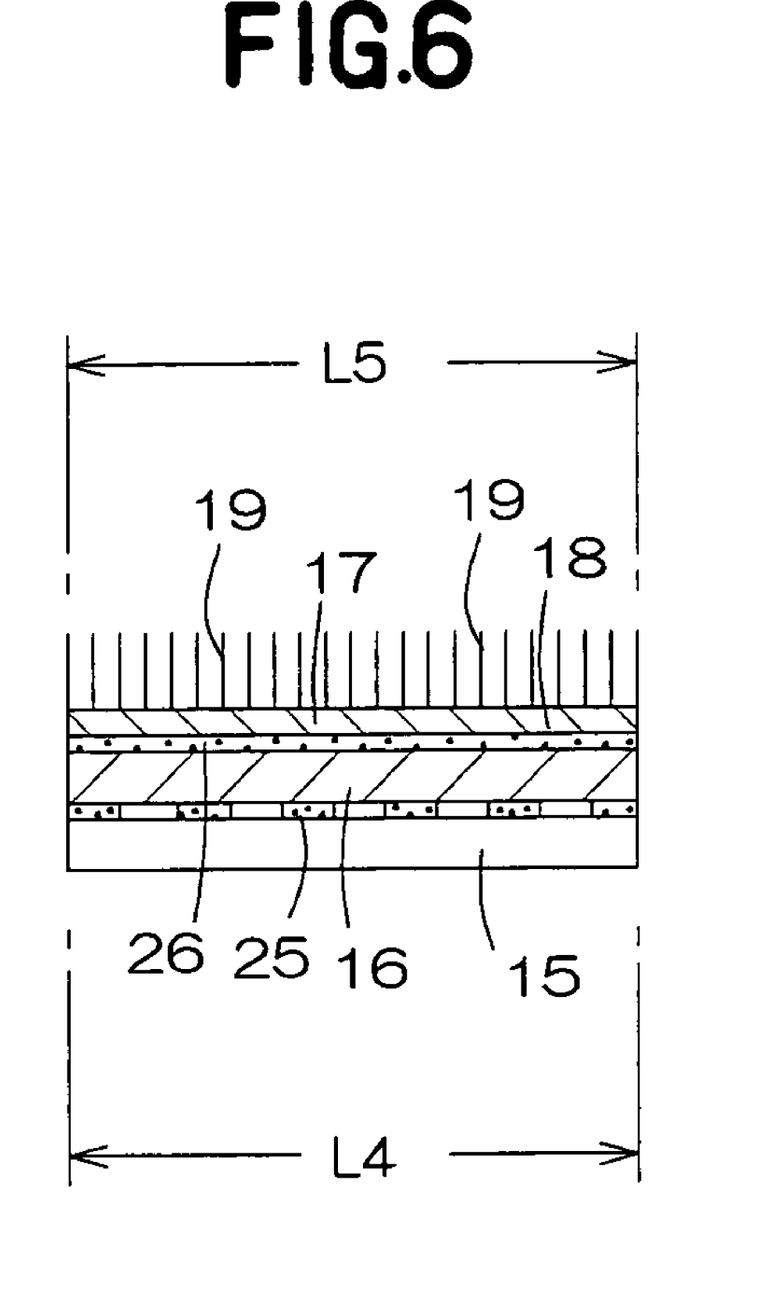
FIG. 6 is a sectional view taken along the line VI-VI in FIG. 4.

FIG. 4 is a partially cutaway perspective view depicting a diaper 1B according to another embodiment of the invention, FIG. 5 is a sectional view taken along the line V-V in FIG. 4 and FIG. 6 is a sectional view taken along the line VI-VI in FIG. 4. In FIG. 4 also, a transverse direction is indicated by an arrow L, a longitudinal direction is indicated by an arrow M and a thickness direction is indicated by an arrow N. A diaper 1B according to this embodiment has as a structure as the diaper 1B of FIG. 1 except for a part thereof. Therefore, components similar to these previously described have the same reference numeral and the description is omitted to avoid the repetition.

In the diaper 1B, the hook members 17 each is disposed in the second zone 29 alone. The first zone 28 is defined by the outer and inner tape strips 15, 16 and the second zone 29 is defined by the inner tape strip 16 and the hook member 17 wherein the tape fasteners 10 each has a stiffness higher in the first zone 28 than in the second zone 29 as the case of the diaper 1A of FIG. 1. The first and second zones 28, 29 of each of the tape fasteners 10 and the outer and inner tape strips 15, 16 and the hook member 17 respectively has as a Gurley stiffness as those in the diaper 1A of FIG. 1. Unlike the case of the diaper 1A of FIG. 1, the first zone 28 is formed by two layers of the outer and inner tape strips 15, 16 and the second zone 29 is also formed by two layers of the inner tape strip 16 and the hook member 17, however, the reason why the second zone 29 has a Gurley stiffness lower than the first zone 28 as the diaper 1A of FIG. 1 is because the outer tape strip 15 having a Gurley stiffness higher than that in the case of the diaper 1A of FIG. 1 is used in the foregoing Gurley stiffness range thereof.

The method used to measure the respective levels of Gurley stiffness of the first and second zones 28, 29, the inner and outer tape strips 15, 16 and the hook member 17 is also the same as the method used for the diaper 1A of FIG. 1. The area of the hook member 17 lying in the second distal portion 24 of the inner tape strip 16 is also the same as for the diaper 1A of FIG. 1. The transverse dimensions L1, L2 of the distal portion 21 and the first distal portion 23 of the outer and inner tape strips 15, 16, respectively, the transverse dimensions L3 of the second distal portion 24 of the inner tape strip 16 and the longitudinal dimensions L4, L5 of the inner and outer tape strips 15, 16, respectively, are the same as those in the diaper 1A of FIG. 1.

Stock materials for the topsheet 2 may be selected from a group consisting of a hydrophilic fibrous nonwoven fabric, a hydrophobic fibrous nonwoven fabric having a plurality of apertures and a plastic film having a plurality of fine perforations. Stock materials for the backsheet 3 and the leak-barrier cuffs 12 may be selected from a group consisting of a hydrophobic fibrous nonwoven fabric, a breathable liquid-impervious plastic film and a composite nonwoven fabric comprising two or more hydrophobic fibrous nonwoven fabric layers laminated one upon another, and a composite sheet comprising a hydrophobic fibrous nonwoven fabric and a breathable liquid-impervious plastic film laminated upon each other. Nonwoven fabrics may be selected from those made by spun lace-, needle punch-, melt blown-, thermal bond-, spun bond- and chemical bond-processes.

Fibrous nonwoven fabrics used to form the top- and backsheets 2, 3, the leak-barrier cuffs 12 and the inner and outer tape strips 15, 16 may be selected from those made by spun lace-, needle punch-, melt blown-, thermal bond-, spun bond- and chemical bond-processes.

As stock materials for the backsheet 3, the leak-barrier cuffs 12 and the inner and outer tape strips 15, 16, it is also possible to use a composite nonwoven fabric (SM nonwoven fabric or SMS nonwoven fabric) consisting of a melt blown fibrous nonwoven fabric having a high water-resistance and a spun bond fibrous nonwoven fabric having a high strength and a high flexibility laminated on at least one side of the melt blown fibrous nonwoven fabric.

The hydrophilic fibrous nonwoven fabric may be made of any one of synthetic fibers, semi-synthetic fibers and regenerated fibers each modified to become hydrophilic or conjugate fibers thereof. The hydrophobic fibrous nonwoven fabric may be formed from synthetic fibers and may contain therein semi-synthetic fibers or regenerated fibers both treated to become water repellent. While not specified, the synthetic fibers may be selected from a group consisting of polyester-, polyacrylonitrile-, polyvinyl chloride-, polyethylene-, polypropylene- and polystyrene-based fibers. The suitably useful synthetic fibers further include core-sheath type conjugate fibers, side-by-side type conjugate fibers, macaroni fibers, microporous fibers and end-to-end type conjugate fibers.

The core 4 comprises a mixture of fluff pulp and super-absorbent polymer particles or a mixture of fluff pulp, super-absorbent polymer particles and thermoplastic synthetic resin fibers, in both cases, compressed to a desired thickness. Preferably, the core 4 is entirely wrapped with a liquid-pervious sheet such as a tissue paper or a hydrophilic fibrous nonwoven fabric in order to prevent the core 4 from getting out of its initial shape. The super-absorbent polymer may be selected from a group consisting of starch-based, cellulose-based and synthetic polymers. Such super-absorbent polymers may be particulate or fibrous.

Permanent bonding of the top- and backsheets 2, 3 to each other, permanent bonding of the leak-barrier cuffs 12 to the top- and backsheets 2, 3, permanent bonding of the core 4 to the top- and backsheets 2, 3 and permanent bonding the elastic members 13, 14, 35 to the top- and backsheets 2, 3 and to the leak-barrier cuffs 12 may be carried out using adhesives or welding techniques such as a heat-sealing or ultrasonic sealing technique. Permanent bonding of the inner and outer tape strips 15, 16 at the respective proximal portions 20, 22 thereof, permanent bonding of the distal portions 21, 23 of the inner and outer tape strips 15, 16, respectively, to each other and permanent bonding of the hook member 17 to the inner tape strip 16 may be carried out selectively using adhesives or welding techniques such as a heat-sealing or ultrasonic sealing technique.

Adhesives may be appropriately selected from a group consisting of a hot melt adhesive, an acrylic adhesive and an elastomeric adhesive. The adhesives may be applied on the top- and backsheets 2, 3 and the leak-barrier cuffs 12 in a suitable pattern selected from a spiral pattern, a zigzag pattern, a dotted pattern and a striped pattern. Application of the adhesives on these elements 2, 3, 12, 15 and 16 in such patterns generates adhesive-coated regions and adhesive-free regions, resulting in that these elements 2, 3, 12 are permanently bonded one to another in intermittent fashion, the elements 15, 16 are permanently bonded to each other and the elements 3, 12, 15 and 16 are bonded to each other, in every case, in an intermittent fashion.

Though not illustrated, it is possible to fold the first and second zones 28, 29 of the tape fastener 10 inward in the transverse direction of the diaper to bring the hooks 19 distributed in these zones 28, 29 in engagement with the outer surface of the proximal portion 22 of the inner tape strip 16 and thereby to temporarily anchor these zones 28, 29 on the proximal portion 22 so far as the inner tape strip 16 is formed from a fibrous nonwoven fabric. It is also possible to use a fibrous nonwoven fabric made of crimped fibers as stock materials for the target zone 11. In this case, the hooks 19 can be effectively engaged with the crimped fibers and thereby the tape fastener 10 can be reliably anchored to the target zone 11.

What is claimed is:

1. A disposable wearing article, comprising:
    a first surface and a second surface opposite to the first surface;
    first and second waist regions, and a crotch region extending in a longitudinal direction of said article between the first and second waist regions;
    a liquid-pervious topsheet adapted to face a wearer's body in use;
    a liquid-impervious backsheet adapted to face away from the wearer's body in use;
    a liquid-absorbent core interposed between said topsheet and said backsheet;
    a pair of water-resistant, longitudinal barrier cuffs each comprising:
        a moveable portion biased to rise above said core, and
        a fixed portion extending in a transverse direction of said article outwardly from an adjacent one of transversely opposite side edges of said core;
    a pair of tape fasteners extending in the transverse direction outwardly from transversely opposite side sections of the first waist region, respectively, each said tape fastener comprising:
        first and second monolithic tape strips disposed on the respective side section so as to sandwich the respective side section therebetween, and
        a hook member attached on one of the first and second monolithic tape strips; and
    a target zone disposed on the first surface in the second waist region and having a plurality of loops releasably engageable with a plurality of hooks of the hook members of said tape fasteners;
    wherein, in each of said tape fasteners,
    the first monolithic tape strip consists of:
        a proximal portion permanently bonded to the first surface in the first waist region at the associated side section, and
        a distal portion contiguous with the proximal portion and extending in the transverse direction outwardly from the associated side section,
    the second monolithic tape strip consists of:
        a proximal portion permanently bonded to the second surface in the first waist region at the associated side section,
        a first distal portion contiguous with the proximal portion of said second monolithic tape strip, extending in the transverse direction outwardly from the associated side section, and being permanently, directly bonded to the distal portion of the first monolithic tape strip, and
        a second distal portion contiguous with the first distal portion, extending in the transverse direction further outwardly beyond an outermost end of the distal portion of the first monolithic tape strip, and being free of direct attachment to the first monolithic tape strip,
    the proximal portions of the first and second monolithic tape strips are permanently bonded to and sandwich therebetween the associated side section which is defined by said backsheet and the fixed portion of an associated one of said barrier cuffs, and
    the hook member is permanently, directly bonded to both the first and second distal portions of the second monolithic tape strip, and is free of direct attachment to the proximal portion of the second monolithic tape strip, whereby the hooks of said hook member are distributed over the first and second distal portions, but not over the proximal portion, of the second monolithic tape strip; and
    wherein each said tape fastener has a stiffness lower in a second zone where the second distal portion of the second monolithic tape strip extends than in a first zone where the distal portion of the first monolithic tape strip extends;

wherein each said tape fastener has a Gurley stiffness in a range of 5.0 to 12 mN in the first zone and a Gurley stiffness in a range of 0.3 to 4.6 mN in the second zone, and wherein, in each of said tape fasteners, the hook member provided on the second distal portion has an area in a range of 1.75 to 8.0 cm$^2$;

an entire dimension, as measured in the transverse direction of the article, of each of said distal portion of the first monolithic tape strip and said first distal portion of the second monolithic tape strip is in a range of 8 to 15 mm; and an entire dimension, as measured in the transverse direction of the article, of said second distal portion of the second monolithic tape strip is in a range of 17 to 22 mm.

2. A disposable wearing article, comprising:

a first surface and a second surface opposite to the first surface;

first and second waist regions, and a crotch region extending in a longitudinal direction of said article between the first and second waist regions;

a liquid-pervious topsheet adapted to face a wearer's body in use;

a liquid-impervious backsheet adapted to face away from the wearer's body in use;

a liquid-absorbent core interposed between said topsheet and said backsheet;

a pair of water-resistant, longitudinal barrier cuffs each comprising:
    a moveable portion biased to rise above said core, and
    a fixed portion extending in a transverse direction of said article outwardly from an adjacent one of transversely opposite side edges of said core;

a pair of tape fasteners extending in the transverse direction outwardly from transversely opposite side sections of the first waist region, respectively, each said tape fastener comprising:
    first and second monolithic tape strips disposed on the respective side section so as to sandwich the respective side section therebetween, and
    a hook member attached on one of the first and second monolithic tape strips; and a target zone disposed on the first surface in the second waist region and having a plurality of loops releasably engageable with a plurality of hooks of the hook members of said tape fasteners;

wherein, in each of said tape fasteners, the first monolithic tape strip consists of:
    a proximal portion permanently bonded to the first surface in the first waist region at the associated side section, and
    a distal portion contiguous with the proximal portion and extending in the transverse direction outwardly from the associated side section, the second monolithic tape strip consists of:
    a proximal portion permanently bonded to the second surface in the first waist region at the associated side section,
    a first distal portion contiguous with the proximal portion of said second monolithic tape strip, extending in the transverse direction outwardly from the associated side section, and being permanently, directly bonded to the distal portion of the first monolithic tape strip, and
    a second distal portion contiguous with the first distal portion, extending in the transverse direction further outwardly beyond an outermost end of the distal portion of the first monolithic tape strip, and being free of direct attachment to the first monolithic tape strip, the proximal portions of the first and second monolithic tape strips are permanently bonded to and sandwich therebetween the associated side section which is defined by said backsheet and the fixed portion of an associated one of said barrier cuffs, and the hook member is permanently, directly bonded to both the first and second distal portions of the second monolithic tape strip, and is free of direct attachment to the proximal portion of the second monolithic tape strip, whereby the hooks of said hook member are distributed over the first and second distal portions, but not over the proximal portion, of the second monolithic tape strip; and wherein each said tape fastener has a stiffness lower in a second zone where the second distal portion of the second monolithic tape strip extends than in a first zone where the distal portion of the first monolithic tape strip extends;

wherein each said tape fastener has a Gurley stiffness in a range of 5.0 to 12 mN in the first zone and a Gurley stiffness in a range of 0.3 to 4.6 mN in the second zone, and wherein, in each of said tape fasteners, a dimension of the proximal portion of the second monolithic tape strip in the transverse direction of the article is greater than that of the proximal portion of the first monolithic tape strip;

the hook member provided on the second distal portion has an area in a range of 1.75 to 8.0 cm$^2$;

an entire dimension, as measured in the transverse direction of the article, of each of said distal portion of the first monolithic tape strip and said first distal portion of the second monolithic tape strip is in a range of 8 to 15 mm; and an entire dimension, as measured in the transverse direction of the article, of said second distal portion of the second monolithic tape strip is in a range of 17 to 22 mm.

* * * * *